US00PP36143P2

(12) United States Plant Patent
Hansen

(10) Patent No.: US PP36,143 P2
(45) Date of Patent: Sep. 24, 2024

(54) ***ALLIUM* PLANT NAMED 'Pincushion'**

(50) Latin Name: ***Allium hybrid* (Linnaeus)**
Varietal Denomination: Pincushion

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/445,587

(22) Filed: Nov. 7, 2023

(51) Int. Cl.
*A01H 5/02* (2018.01)
*A01H 6/04* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt

(57) ABSTRACT

A new and distinct cultivar of *Allium* plant named 'Pincushion', with glaucous, upright, stiff, strap-like, slightly-twisted green foliage, and numerous, tightly-clustered, light lavender-purple flowers forming in densely-arranged globose umbels over a long period beginning in early August. Strong stems hold the flower heads upright through flowering and seed production. The new plant is deer and rabbit-resistant and makes an attractive plant for the garden.

2 Drawing Sheets

Botanical classification: *Allium* hybrid (Linnaeus).
Variety denomination: 'Pincushion'.

STATEMENT REGARDING PRIOR DISCLOSURES UNDER 37 CFR 1.77(b)(6)

The first public sale or offer for sale was by Walters Gardens, Inc. on Nov. 8, 2022. The claimed plant was first listed on a website operated by Walters Gardens, Inc., on Feb. 1, 2023, followed by the disclosure in the Walters Gardens 2023-2024 Catalog' on May 19, 2023. Walters Gardens, Inc. obtained the plant and all information relating thereto, from the inventor. No plants of *Allium* 'Pincushion' have been sold or offered for sale in this country or anywhere in the world, nor has any disclosure of the new plant been made, more than one year prior to the filing date of this application, and such sale or disclosure within one year was either derived directly or indirectly from the inventor.

BACKGROUND AND ORIGIN OF THE PLANT

The present invention relates to the new and distinct ornamental onion, *Allium* 'Pincushion' was hybridized by the inventor at a wholesale perennial nursery in Zeeland, Michigan, USA as the result of a greenhouse cross between the proprietary unreleased selection known as 14-SP-ALL-311 (not patented) and 'Nor'easter' (not patented) on Jun. 23, 2014. Seeds from this pollination were collected in the fall of 2014 and were sown later the same year. The plant from a single seedling was originally evaluated in the summer of 2016, selected for further evaluation, and given the breeder code 14-1-5.

*Allium* 'Pincushion' has been successfully asexually propagated by garden bulb division method since 2016 at a wholesale perennial nursery in Zeeland, Michigan, and found to be stable and produce identical plants that maintain the unique characteristics of the original plant through multiple generations.

SUMMARY OF THE PLANT

*Allium* 'Pincushion' differs from its parents as well as all other ornamental onion known to the applicant. The most similar known *Allium* cultivars are: *Allium senescens* 'Blue Eddy' (not patented), 'Medusa' U.S. Plant Pat. No. 28,701, *Allium tanguticum* 'Summer Beauty' (not patented), 'Lavender Bubbles' U.S. Plant Pat. No. 31,126, 'Serendipity' U.S. Pat. No. 32,023, and 'Millenium' (not patented).

'Blue Eddy' has shorter and more twisted foliage, the habit is smaller, the plant has fewer inflorescences that droop prior to opening, the inflorescence is a smaller globe, and flowers are lighter colored. 'Medusa' has taller inflorescences that begin in bud drooping over and straighten when flowers starting to open and the foliage is more twisted. 'Summer Beauty' has lighter-colored flowers in larger and taller umbels and produces no seed. 'Lavender Bubbles' has a larger habit and blooms later with larger inflorescences of light lilac-purple flowers. 'Serendipity' has larger flower heads with more flowers, the flowers have a darker hue, and the habit is larger. 'Millenium' has foliage that is broader, longer, and less glaucous blue-green, and the flowers are of a lighter hue in larger and taller umbels with more flowers.

The female parent, 14-SP-ALL-311, has larger flower heads with more flowers, the flowers have a darker hue, the habit is larger, and the foliage is variegated. The male parent, 'Nor'easter', has broader more bluish foliage and white flowers.

Each of the parents and above comparison cultivars has less stiffly upright foliage and less densely arranged flower heads.

*Allium* 'Pincushion' differs from these above cultivars and all unregistered cultivars known to the inventor in that it has:

1. Glaucous, upright, stiff, strap-shaped, slightly-twisted, green foliage;
2. Compact habit, drought tolerant, and deer resistant, medium-sized clumps;
3. Numerous, tightly-clustered, light lavender-purple flowers forming dense globose umbel;
4. Strong stems hold flower heads upright through flowering and seed production.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source, and direction may cause the appearance of minor variations in color.

DETAILED BOTANICAL DESCRIPTION

Figure 1:
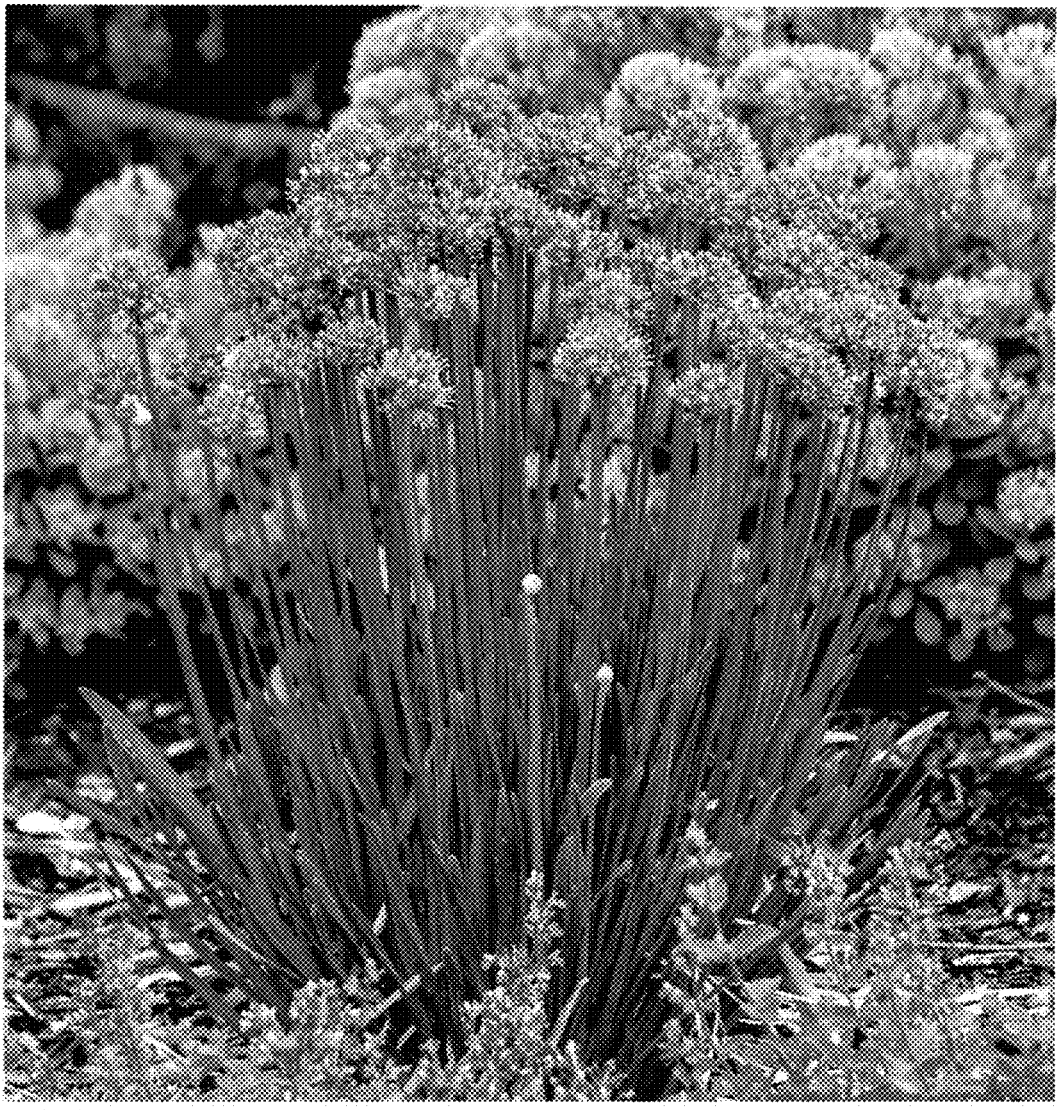
FIG. 1 shows the side-view habit of a three-year-old plant in early flowering.
Figure 2:
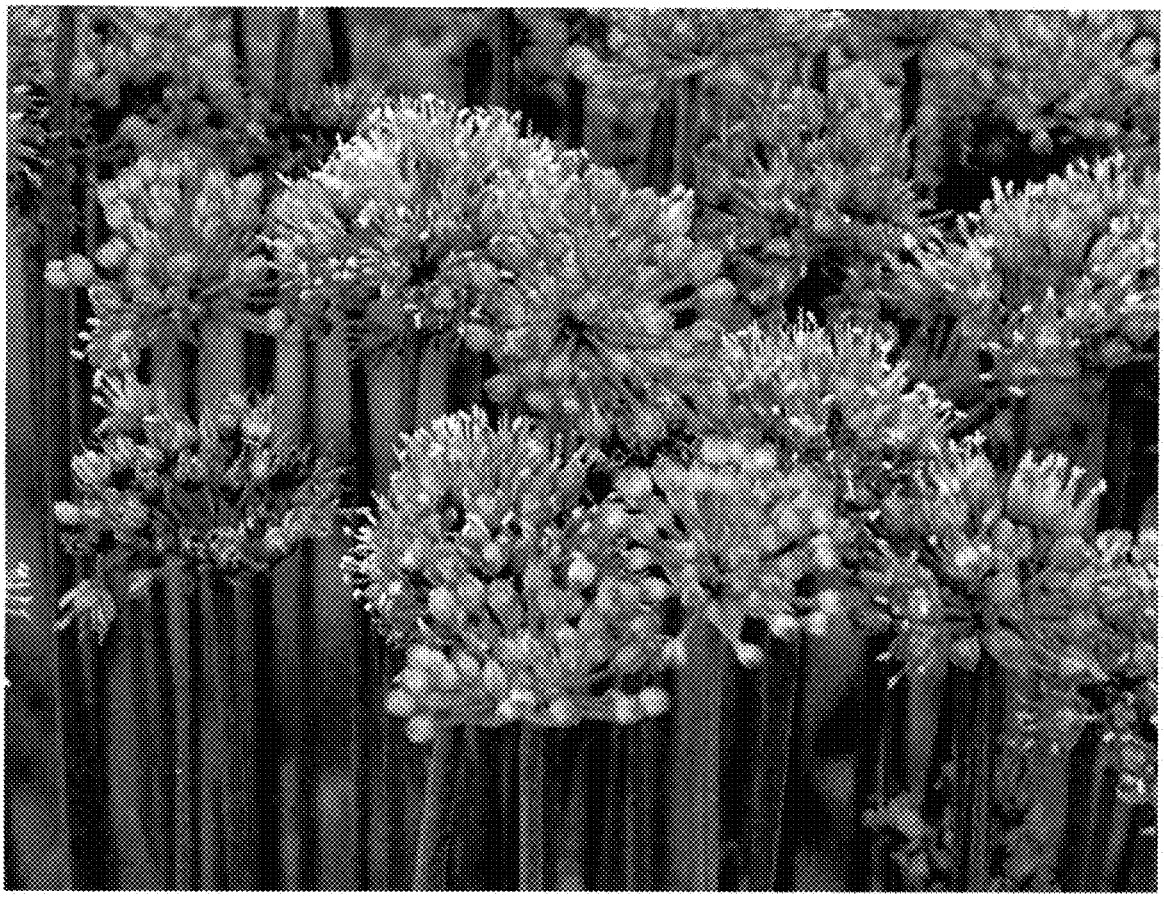
FIG. 2 shows a close-up of the umbels with flowers and buds.

The following descriptions and color references are based on the 2015 edition of The Royal Horticultural Society Colour Chart except where common dictionary terms are used. The new plant, *Allium* 'Pincushion', has not been observed under all possible environments. The phenotype may vary slightly with different environmental conditions, such as temperature, light, fertility, moisture, and maturity levels, but without any change in the genotype. The following observations and size descriptions are of a three-year-old plant in a trial garden of a wholesale perennial nursery in Zeeland, Michigan under full sun with supplemental water and fertilizer as needed.

Botanical classification: *Allium* hybrid;

Parentage: Female or seed parent was 14-SP-ALL-311, the male or pollen parent was 'Nor'easter';

Propagation method: By garden bulb division;

Growth rate: Vigorous, flowering in 4-liter containers in about 12 weeks;

Rooting habit: Fibrous from base of bulbs, lightly branching; color nearest RHS 158C;

Plant habit description: Dense clump of bulbs with stiffly upright sessile, rosulate foliage about 54 cm across with leaves spreading later in the season and about 26 cm tall; flowering to about 39 cm tall;

Bulbs: Elongated conical shape; about 6 cm long and 1.5 cm diameter at base; average about 80 per plant; color nearest RHS 155D;

Leaves: sessile; linear; glaucous, glabrous dull surfaces; semi-succulent; simple; margin entire; sharply acute apex, truncate base; slightly twisted longitudinally, about 360°; mostly flat; about 25 cm long, about 5 mm across near middle and to about 2 mm thick near middle; arranged in two-ranked tuffs from bulb; about 8 leaves per bulb; fragrance onion-scented;

Leaf color: Expanding leaves adaxial and abaxial base nearest RHS 157D, distally adaxial and abaxial nearest RHS 137A; mature leaves adaxial and abaxial base nearest RHS NN15SC, distally adaxial and abaxial nearest RHS 137A;

Leaf venation: Parallel; color nearest RHS 137A adaxial and abaxial;

Inflorescence: Terminal umbel; round; with flowers aspect upwardly and outwardly; about 53 mm diameter; about 40 flowers per umbel; about 70 to 100 inflorescences per plant;

Flowering period: Beginning early August for about four weeks; individual umbels effective for about 18 days;

Blooming habit: With upright semi-globe in bud stage, remaining upright as initial flowers open; one terminal umbel inflorescence per stem;

Buds one day prior to opening: Ellipsoidal; about 7 mm long and 4 mm diameter at middle;

Bud color: Nearest RHS 84D in proximal 3 mm with apex between RHS N75A and RHS N78A;

Flowers: Campanulate; incomplete; perfect; with two sets of three tepals, outer set smaller than inner; inferior ovary; actinomorphic; upward and outwardly facing depending on the position in umbel; individually effective about four to six days;

Flower size: From base to exerted stamens to about 9.5 mm long and about 6 mm across;

Tepals (outer set): Lanceolate to deltoid; concavo-convex; glabrous; slightly lustrous; acute apex, fused truncate base; about 5 mm long and about 2 mm across;

Tepal (inner set): Ovate to deltoid; flat; glabrous; lustrous; acute apex, broadly acute base; about 5.5 mm long and about 2.5 mm across;

Tepal color (outer set): Upon first opening-adaxial base nearest RHS NN155D, middle and apex between RHS 85C and RHS 84C; abaxial nearest RHS NN155D, middle and apex between RHS 85C and RHS 84C; at maturity-adaxial between RHS N81C and RHS N82C and abaxial between RHS N81D and RHS 81D;

Tepal color (inner set): Upon first opening-adaxial nearest RHS NN155D, middle and apex between RHS 85C and RHS 84C; abaxial nearest RHS NN155D, middle and apex between RHS 85C and RHS 84C; at maturity-adaxial between RHS N81C and RHS N82C and abaxial longitudinal center between RHS N81B and RHS N82B with the surrounding area between RHS N81D and RHS N82D;

Pedicel: Cylindrical; stiff, upwardly and outwardly facing depending on orientation in umbel; glabrous; glaucous; about 18 mm long and about 0.7 mm diameter;

Pedicel color: Nearest RHS 146C;

Peduncle: Glabrous, glaucous; slightly applanate, flattened trapezoid in cross-section; with longitudinal ridges; about 32.5 cm long, base about 5 mm wide and about 4 mm thick;

Peduncle color: Basal 10 mm nearest RHS 138B and distally between RHS 138A and RHS 137B;

Gynoecium: Pistil single; when first open to about 5 mm, expanding to about 8 mm long with maturity;

*Style*.—Single, cylindrical, glabrous, to about 5.5 mm long and about 0.3 mm across when mature; color nearest RHS 84C.

*Stigma*.—Globose; about 0.2 mm across; color lighter than RHS 76D.

*Ovary*.—Trilocular; locules adnate along center axis, obcordate; individually about 2 mm long and 1.5 mm across middle, and together about 3 mm across; rounded apex and truncate base; color initially between RHS 85C and RHS 84C lightening to between RHS N187D and RHS 84D.

Androecium: Six; exserted to about 9 mm long;

*Anther*.—Oblong ellipsoidal; about 2 mm long and about 1.2 mm wide; basifixed; longitudinal; color between RHS N200C and RHS N187C.

*Filament*.—Exserted; glabrous; cylindrical; about 9 mm long, 1.2 mm across at base, and 0.5 mm diameter at top; color nearest RHS 84A.

*Pollen*.—Abundant; color nearest RHS N200D.

Receptacle: Turbinate; about 2 mm tall and 2 mm across top, tapering to pedicel; color nearest RHS 138A;

Fruit: Tri-valved loculicidal capsule; about 5 mm long and 4 mm across; typically dehiscing to within about 10 mm of base; one to three seeded; color upon maturity nearest RHS 199D;

Seed: Elliptic, flattened along one long side; about 2.5 mm long and about 1.5 mm across; color nearest RHS 202A;

Disease and pest resistance: Ornamental onions typically resist deer feeding. Resistance beyond that of other ornamental onions has not been observed. *Allium* 'Pincushion' plants grow best with good drainage and are able to tolerate some drought when established.

Hardiness at least from USDA zone 4 through 8.

I claim:

1. A new and distinct cultivar of *Allium* plant named 'Pincushion', as herein described and illustrated.

* * * * *